US006586246B1

(12) United States Patent
Yoon et al.

(10) Patent No.: US 6,586,246 B1
(45) Date of Patent: Jul. 1, 2003

(54) PREPARING POROUS BIODEGRADABLE POLYMERIC SCAFFOLDS FOR TISSUE ENGINEERING USING EFFERVESCENT SALTS

(75) Inventors: Jun-Jin Yoon, Seoul (KR); Tae-Gwan Park, Daejeon (KR); Yoon-Sung Nam, Seoul (KR)

(73) Assignee: Innotech Medical, Inc., Daejon (KR)

( * ) Notice: Subject to any disclaimer, the term of this patent is extended or adjusted under 35 U.S.C. 154(b) by 0 days.

(21) Appl. No.: 09/700,458
(22) PCT Filed: Feb. 12, 2000
(86) PCT No.: PCT/KR00/00106
§ 371 (c)(1), (2), (4) Date: Feb. 6, 2001
(87) PCT Pub. No.: WO00/55300
PCT Pub. Date: Sep. 21, 2000

(30) Foreign Application Priority Data

Mar. 18, 1999 (KR) .............................................. 99-9263
Nov. 16, 1999 (KR) ............................................ 99-50922

(51) Int. Cl.$^7$ ............................ C12N 5/06; C12N 5/08; C12N 11/08; A61F 2/00
(52) U.S. Cl. ....................... 435/396; 424/426; 435/180; 435/395; 435/397
(58) Field of Search ................................ 435/174, 177, 435/180, 395, 396, 397; 424/423, 426, 93.7

(56) References Cited

U.S. PATENT DOCUMENTS 5,939,323 A  * 8/1999  Valentini et al. ............. 435/395
6,143,293 A  * 11/2000 Weiss et al. ................ 424/93.7
6,165,486 A  * 12/2000 Marra et al. ................ 424/423

* cited by examiner

Primary Examiner—David M. Naff
(74) Attorney, Agent, or Firm—Howard & Howard

(57) ABSTRACT

Three-dimensional porous biodegradable and biocompatible, polymeric scaffolds for tissue engineering are prepared by a method involving effervescing of an effervescent salt in a gel to result in a porous structure. A polymer is dissolved in an organic solvent to prepare a polymer solution of high viscosity. Optionally, the polymer solution is mixed with an organic solvent that does not dissolve the polymer to concentrate the solution. An effervescent salt is homogeneously mixed with the polymer solution to give a polymer/salt/organic solvent mixed gel. The organic solvent is removed from the mixed gel to produce an organic solvent-free polymer/salt gel slurry. The gel slurry is submerged in a hot aqueous solution or acidic solution to cause the salt to effervesce at room temperature to form a porous three-dimensional polymeric structure. The polymeric structure is washed with distilled water and freeze-dried to yield a scaffold that is suitable for cell or tissue culture. Pore size and porosity of the scaffold can be easily controlled by controlling the size and amount of the effervescent salt and concentration of the acidic solution.

12 Claims, 9 Drawing Sheets

PREPARING POROUS BIODEGRADABLE POLYMERIC SCAFFOLDS FOR TISSUE ENGINEERING USING EFFERVESCENT SALTS

TECHNICAL FIELD

The present invention relates, in general, to a method for preparing three-dimensional porous scaffolds which can be used as supports or culture matrices for in-vitro tissue culture and, more particularly, to the use of effervescent salts in preparing scaffolds through a gel phase, thereby allowing the scaffolds to be molded in desirable forms and to have a desirable pore size and porosity.

PRIOR ART

To be used for bio-tissue culture, polymers are basically required to be of biocompatibility and biodegradability. The aliphatic polyesters which bear lactic acid or glycolic acid as a backbone unit were approved as being satisfactory to the requirement by the Food and Drug Administration (FDA), U.S.A., and most widely used now. Examples of such biocompatible and biodegradable aliphatic polyesters include poly(lactic acid) (PLA) poly(glycolic acid) (PGA), poly(D,L-lactic-co-glycolic acid) (PLGA), poly (caprolactone), poly(valerolactone), poly(hydroxybutyrate), poly(hydroxy valerate), etc.

Proven to be biocompatible, the aliphatic polyesters have been widely used as drug delivery carriers or sutures for a long period of time.

PLGA is found to afford biodegradable polymers with various degradation periods by controlling the ratio of lactic acid monomer and glycolic acid monomer and/or modifying the synthesis procedure thereof.

In addition to biodegradability and biocompatibility, other requirements for the polymers for bio-tissue culture are a surface area large enough to allow cell adhesion at high densities, a pore size large enough to enable the vascularization in the cultured tissue after transplantation into a host and the transmission of substances, such as nutrients, growth factors and hormones, and the interconnectivity of the pores.

Typically, the porous polymeric scaffolds fulfilling the above requirements are prepared as follows.

The most popular and commercially available are scaffolds consisting of PGA sutures (unwoven PGA fiber mesh). They are made in three-dimensional shapes by thermally treating randomly entangled threads of suture. The mesh exhibits very high porosity and sufficiently large pore size in addition to being of high interconnectivity, but finds a limited range of applications on account of poor mechanical strength (see: A. G. Mikos, Y. Bao, L. G. Cima, D. E. Ingber, J. P. Vacanti, and R. Langer, J. Biomed. Mater. Res. (1993) 27, 183–189).

Another preparing method of the porous polymeric scaffolds is of particulate leaching, favored by A. G. Mikos et al. (See: A. G. Mikos, G. Sarakinos, S. M. Leite, J. P. Vacanti, and R. Langer, Biomaterials (1993) 14, 5, 323–330; A. G. Mikos, A. J. Thorsen, L. A. Czerwonka, Y. Bao, R, Langer, D. N. Winslow, and J. P. Vacanti, Polymer (1994) 35, 5, 1068–1077). The particulate leaching method has an advantage of easily controlling pore sizes of the scaffolds in dependence on the size of the salt (NaCl) employed, but suffers from a disadvantage in that salts remaining in the scaffolds or their rough morphology cause cell damage.

Besides, an emulsion freeze-drying method and a high pressure gas expansion method can be used for the preparation of such scaffolds (see: k. Whang, C. H. Thomas, K. E. Healy, G. Nuber, Polymer (1995) 36, 4, 837–842; J. J. Mooney, D. F. Baldwin, N. P. Suh, J. P. Vacanti, and R. Langer, Biomaterials (1996) 17, 1417–1422). Despite their own advantages, the methods have the limitation of there being difficulties in making open cellular pores.

In recent, attempts have been made to construct the scaffolds by taking advantage of the phase separation of polymer solutions (H. Lo, M. S. Ponticiello, K. W. Leong, Tissue Eng. (1995) 1, 15–28; H. Lo, S. Kadiyala, S. e. Guggino, K. W. Leong, J. Biomed. Mater. Res. (1996) 30, 475–484; Ch. Schugens, V. Maguet., Ch, Grandfils, R. Jerome, Ph. Teyssie, J. Biomed. Mater. Res. (1996) 30, 449–461).

As mentioned above, various methods have been developed for the preparation of three-dimensional polymeric scaffolds in which cell adhesion and differentiation can be induced. Nevertheless, there remain problems to be solved in preparing three-dimensional scaffolds for tissue culture with biodegradable polymers. At present, only a few companies, such as Advanced Tissue Science Inc. and Texas Biotechnology Inc. have been successful in the commercialization of such scaffolds, wherein PGA suture is utilized on a small scale.

DISCLOSURE OF THE INVENTION

It is an object of the present invention to overcome the above problems encountered in prior arts and to provide a method for preparing biodegradable, three-dimensional, porous scaffolds for tissue culture, whereby the scaffolds can be molded in desirable forms and have desirable pore sizes and porosities.

Based on the present invention, the above object could be accomplished by a provision of a method for preparing biodegradable, three-dimensional, porous scaffolds for tissue culture, comprising the steps of dissolving a biodegradable polymer in an organic solvent to prepare a polymeric solution of high viscosity, homogeneously mixing an effervescent salt in the polymeric solution to give a polymer/salt/organic solvent mixed gel, removing the organic solvent from the polymer/salt/organic solvent mixed gel, submerging the organic solvent-free polymer/salt gel slurry in a hot aqueous solution or acidic solution to render the salt to effervesce at room temperature to afford a three-dimensional polymeric structure, and washing with distilled water and freeze-drying the polymeric structure.

BRIEF DESCRIPTION OF THE DRAWINGS

The above and other objects, features and other advantages of the present invention will be more clearly understood from the following detailed description taken in conjunction with the accompanying drawings, in which:

FIG. 2b is a magnified photograph of FIG. 2a;

FIG. 4b is a magnified photograph of FIG. 4a;

FIG. 5b is a magnified photograph of FIG. 5a;

BEST MODES FOR CARRYING OUT THE INVENTION

Figure 1A:
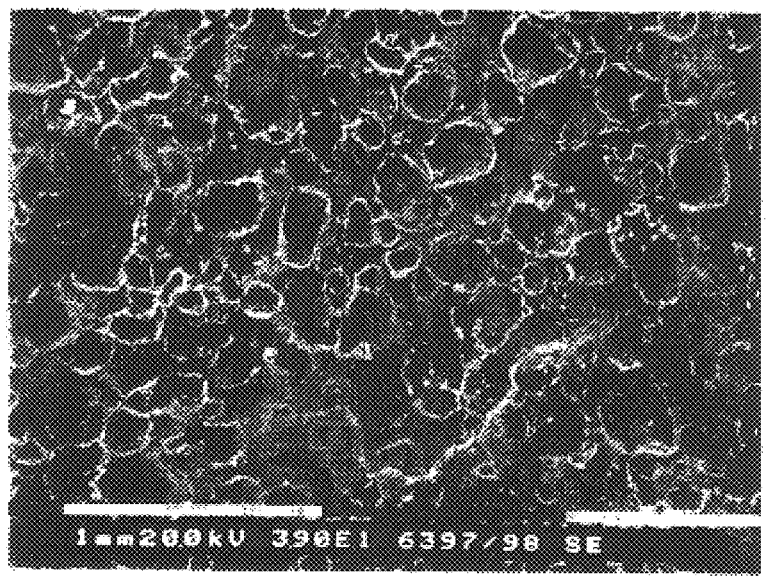
FIGS. 1a and 1b are SEM photographs showing the surface structure (1a) and the cross section structure (b) of the poly(L-lactic acid) based scaffold prepared in Example I.

Before the present method for preparing (title of the invention) are disclosed or described, it is to be understood that the terminology used herein is for the purpose of describing particular embodiments only and is not intended to be limiting. It must be noted that, as used in the specification and the appended claims, the singular forms "a", "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

In the present invention, the preparation of biodegradable and biocompatible, three-dimensional, porous scaffolds for tissue culture is based on phase separation and particulate leaching. First, a biodegradable and biocompatible polymer is dissolved in an inorganic solvent to give a highly concentrated solution with high viscosity. Optionally, the polymer solution is further mixed with an organic solvent which does not dissolve the polymer, so as to concentrate the solution into a gel phase of a concentrated solution. By doing this, it is possible to prepare porous polymeric scaffolds even with biodegradable, low-molecular weight polymers which cannot be conventionally used as materials on account that their solutions are of low viscosity even at high concentrations. Then, the polymeric solution is homogeneously mixed with an effervescent salt, followed by the removal of the organic solvent from the resulting polymer/salt/organic solvent mixed gel. Submergence of the organic solvent-free polymeric/salt gel slurry in a hot aqueous solution or acidic solution effervesces the salt, resulting in a porous structure. Subsequently, this structure is washed with distilled water and freeze-dried to yield a scaffold, which is suitable for cell or tissue culture.

Useful as the biodegradable and biocompatible polymer in the present invention is one selected from the group consisting of poly(L-lactic acid) (PLLA), amorphous poly (D,L-lactic acid) (PDLLA), poly(glycolic acid), poly(D,L-lactic-co-glycolic acid) (PLGA), poly(caprolactone), poly (hydroxy butyrate), and copolymers of these polymers. They may be used irrespective of molecular weight, but better results are obtained from those whose molecular weight is in the range of 5,000–500,000.

Examples of the organic solvent for use in dissolving the biodegradable polymers include methylene chloride, chloroform, acetone, dimethylsulfoxide, dimethylformamide, N-methylpyrrolidone, dioxane, tetrahydrofluran, ethylacetate, methylethylketone, and acetonitrile. Incapable of dissolving the biodegradable polymer, the organic solvent used for the concentration of the polymeric solution is exemplified by ethanol, methanol, aqueous ethanol, ethyl ether, diethyl ether, hexane, petroleum ether, and aqueous petroleum ether.

With a size of 100–500 μm, the effervescent salt is selected from the group consisting of ammonium carbonate, ammonium bicarbonate, sodium carbonate, and sodium bicarbonate. It is preferred to use the salt at such an amount that the weight ratio of the polymer to the effervescent salt may be in the range from 1:1 to 1:100.

Depending on the organic solvent remaining in the polymer/salt/organic solvent mixed gel, various methods may be utilized to remove the organic solvent. Organic solvents with relatively low boiling points, such as methylene chloride, chloroform and dioxane, are removed through drying at ordinary pressure or under vacuum while high-boiling point solvents, such as dimethylsulfoxide (DMSO) and methylpyrrolidone, are replaced with low boiling point solvents, such as ethanol and methanol, before being dried at atmospheric pressure or under vacuum.

In order to effervesce the salt of the polymer/effervescent salt slurry, hot distilled water or acidic aqueous solutions are used. It takes a lengthy period of time to conduct the effervescence of the salt with tepid, distilled water. If the temperature of the distilled water is raised, the reaction time can be reduced. The temperature needs not to be particularly limited, but may be selected according to the judgement of those who are skilled in the art. On the other hand, acidic aqueous solutions enable the salt to effervesce at room temperature within a short period of time. In addition, their concentrations affect the size of the pores formed in the scaffolds, so that the pore size can be under the control of the concentration. Therefore, the effervescence of the salt with the acidic aqueous solutions makes it possible to prevent the thermal distortion of the polymer and to form pores at desirable sizes as well as to settle down inside the porous scaffold the drugs necessary for cell culture.

Available in the effervescence of the present invention is the acid selected from the group consisting of citric acid, hydrochloric acid, acetic acid, formic acid, tartaric acid, salicylic acid, benzoic acid, and glutamic acid. For use, these acids are dissolved to the concentration of 1% or supersaturation in water or in an aqueous solution saturated with an organic solvent, such as methylene chloride, chloroform, dioxane, dimethylsulfoxide (DMSO), and methyl pyrrolidone.

A better understanding of the present invention may be obtained in light of the following examples which are set forth to illustrate, but are not to be construed to limit the present invention.

EXAMPLE I

Preparation of Porous Scaffold from Poly(L-lactic Acid)

In methylene chloride was dissolved PLLA with a weight average molecular weight of 300,000 at a weight ratio of 1:6

PLLA:methylene chloride. The resulting polymeric solution was increased in viscosity by the evaporation of the solvent under the atmospheric pressure. To the concentrated polymeric solution, ammonium bicarbonate with a size distribution of 100–500 μm was added at a mass ratio of 1:6 polymer:salt, followed by homogeneously mixing to yield a polymer/salt/solvent gel.

After being introduced into a brass mold which was 3 mm thick with a diameter of 25 mm, the gel was deprived of the solvent methylene chloride by evaporation under the atmospheric pressure. The polymer/salt mixture separated from the mold was desalted at a vacuum ($9 \times 10^{-6}$ Torr) for 14 days and then, submerged in distilled water of 40° C. to completely leach out the remaining salt.

The salt-free polymeric scaffold thus obtained was dried in a vacuum drier and measured for porosity and total pore volume with the aid of mercury intrusion porosimetry (Porous Materials, Inc., Ithaca, N.Y.). The results are given in Table 1, below.

TABLE 1

Porosity and Total Pore Volume of Polymeric Scaffold

| Salt:Polymer (weight ratio) | Salt Size (μm) | Porosity (%) | Pore Volume (cm³/g) |
|---|---|---|---|
| 6:1 | 100–500 | 86.60 | 7.82 |

Figure 1B:
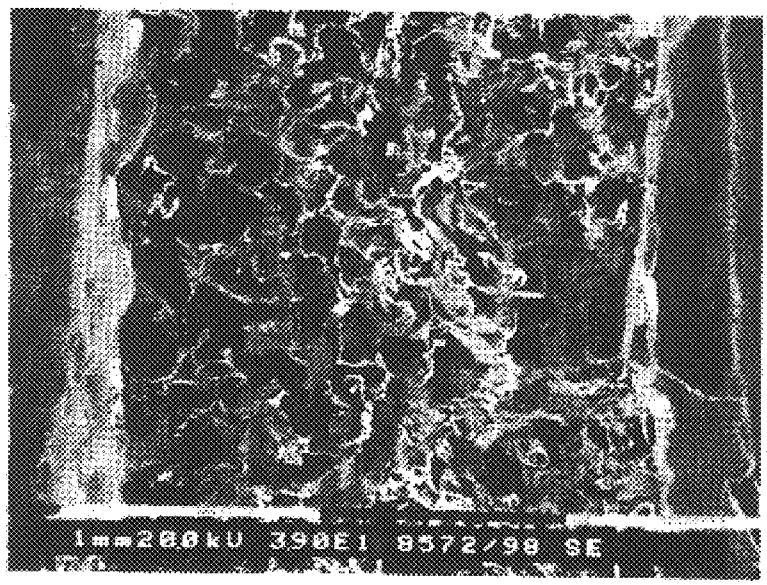

Using a sputter (Hummers, techniques U.S.A.), the polymeric scaffold was coated with gold in an argon atmosphere at 5 psi for 5 min under an electric field of 5 mA. The scaffold was photographed for its whole figure, structures of surface and cross section, and configuration of inner pores by use of a scanning electron microscopy (SEM) (Phillips 535M) and these are shown in FIGS. 1a and 1b.

EXAMPLE II

Preparation of Porous Scaffold from Poly(L-lactic Acid)

In chloroform, PLLA with a weight average molecular weight of 300,000 was dissolved at a weight ratio of PLLA:chloroform ranging 1:10 to 1:20. To the resulting polymeric solutions of high viscosity, ammonium bicarbonate particles which had size distributions of 100–180 μm, 180–300 μm and 300–500 μm, were added at mass ratios of 1:10, 1:15 and 1:20 polymer:salt, respectively, followed by homogeneously mixing to yield polymer/salt/solvent gels.

After being introduced into a Teflon mold which was 1.1 mm thick with a diameter of 5 mm, the gels each were deprived of the solvent methylene chloride by evaporation under the atmospheric pressure. The polymer/salt mixtures separated from the mold were submerged in 3 liters of distilled water maintained at 90° C. to effervesce the salts to give polymeric scaffolds. The salt-free polymeric scaffolds thus obtained were dried in a vacuum drier.

Figure 2A:
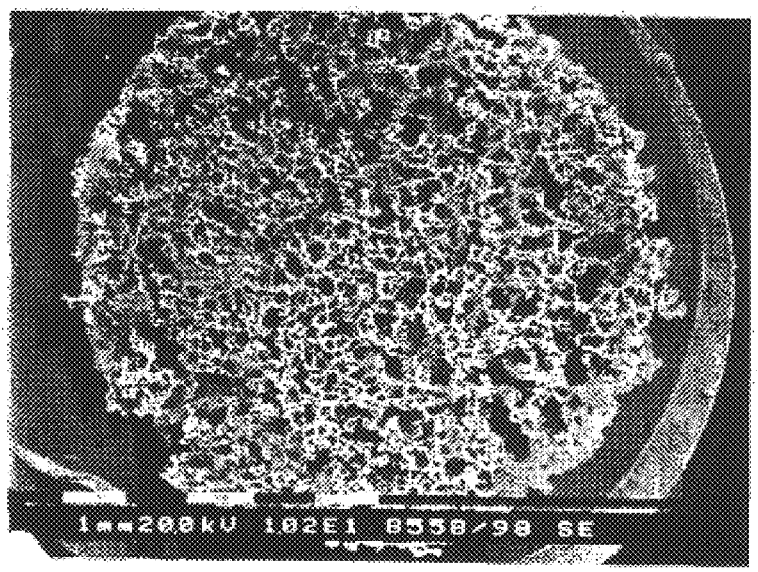
FIG. 2a is a SEM photograph showing the surface structure of the poly(L-lactic acid) based scaffold prepared using a weight ratio of 10:1 salt:polymer in Example II
Figure 2B:
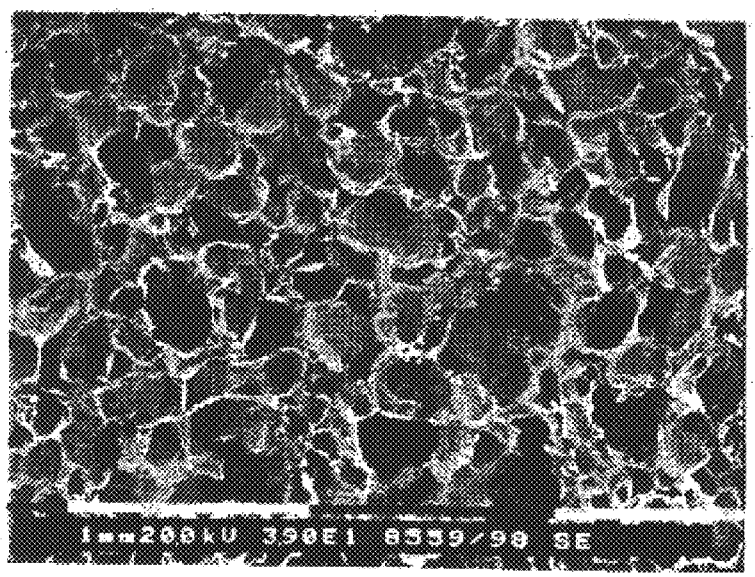
Figure 2C:
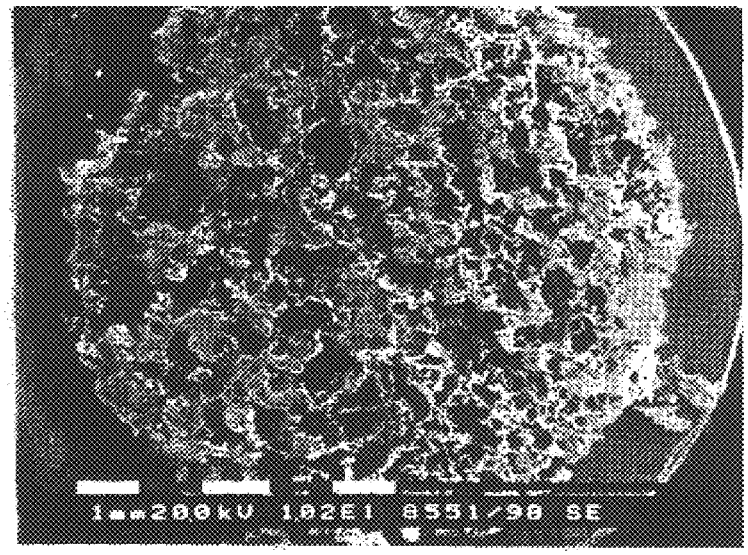
FIG. 2c is a SEM photograph showing the surface structure of the poly(L-lactic acid) based scaffold prepared using a weight ratio of 20:1 salt:polymer in Example II
Figure 2D:
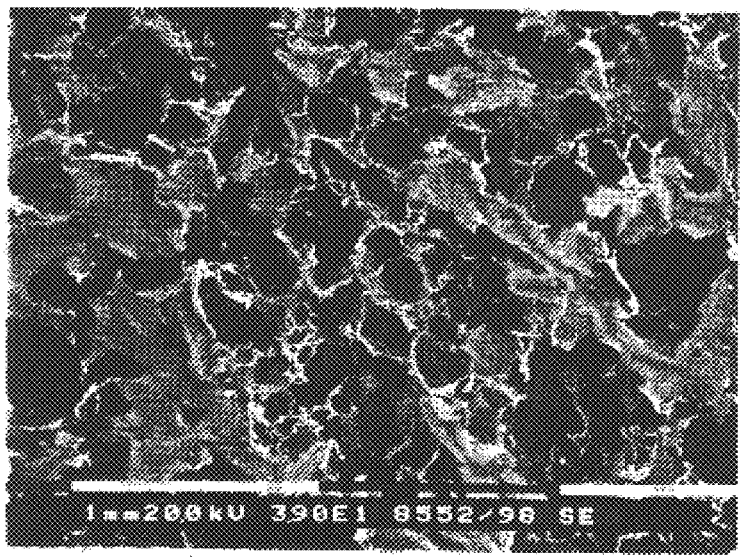
FIG. 2d is a magnified photograph of FIG. 2c.

Using a sputter (Hummers, techniques U.S.A.), the polymeric scaffolds were coated with gold in an argon atmosphere at 5 psi for 5 min under an electric field of 5 mA. The scaffold was photographed for its whole figure, structures of surface and cross section, and configuration of inner pores by use of a scanning electron microscopy (SEM) (Phillips 535M) and the surface and cross section structures of the polymeric scaffolds are shown in FIG. 2. FIGS. 2a and 2b are for the scaffold utilizing the mass ratio of 1:10 PLLA:salt while FIGS. 2c and 2d are for the mass ratio of 1:20 PLLA:salt. As seen in these photographs, higher salt ratios result in larger pore sizes.

The change of thermal properties in the polymeric scaffold was analyzed with the aid of a differential scanning calorimeter, such as that sold by DuPont, identified as Model 2000, while the temperature of the scaffold was raised at an elevation rate of 10° C./min from –10° C. to 200° C.

In a first heating round, the polymeric scaffold and a polymer powder made of the same material were measured for melting point (Tm) and enthalpy change (ΔHm) at melting point while a measurement was made of glass transition temperature (Tg) in a second heating round. The results are given in Table 2, below. As apparent from the data, not so large differences in the thermal properties of interest are found between the polymeric scaffold and the PLLA powder, indicating that the thermal properties of the polymer are not changed during the preparation of the polymeric scaffold.

TABLE 2

Thermal Properties of Polymeric Scaffold

| Materials | Tg (° C.) | Tm (° C.) | Enthalpy (J/g) |
|---|---|---|---|
| Polymer Powder | 62.65 | 177.17 | 34.50 |
| Scaffold | 62.47 | 177.55 | 34.36 |

With the aid of a mercury intrusion porosimetry, the salt-free polymeric scaffolds were measured for porosity and total pore volume, and the results are given in Table 3, below.

TABLE 3

Porosities and Pore Volumes of Polymeric Scaffolds

| Salt:Polymer (weight ratio) | Salt Size (μm) | Porosity* (%) | Porosity** (%) | Pore Volume (cm³/g) |
|---|---|---|---|---|
| 10:1 | 100–180 | 90.57 | 89.21 | 11.42 |
| 10:1 | 180–300 | 92.04 | 89.89 | 12.62 |
| 15:1 | 180–300 | 93.61 | 91.96 | 15.18 |
| 20:1 | 180–300 | 95.12 | 93.49 | 19.21 |
| 10:1 | 300–500 | 93.52 | 91.15 | 11.94 |

*results from the measurement of weights and volumes of scaffolds
**results from the measurement of a mercury intrusion porosimetry The data of Table 3 demonstrate that the porosity and total pore volume of the scaffold increase with the increasing of the salt ratio, but do not depend largely on the size of the salt used.

A measurement was also made of the compression of modulus of the porous polymeric scaffolds prepared above. In this regard, the Instron 5538 was used to descend a load cell of 10 newton (N) at a speed of 2 mm/min vertically on a scaffold specimen, which was of a cylindrical shape 12 mm high with a diameter of 6 mm according to ASTM F451-95. The results are given, along with the porosity, in Table 4, below.

TABLE 4

Compression of Modulus of Polymeric Scaffold

| Salt:Polymer (Weight Ratio) | Porosity (%) | Compression of Modulus (kPa) |
|---|---|---|
| 10:1 | 90.68 | 243 ± 32.5 |
| 20:1 | 95.20 | 65.8 ± 5.4 |

It is apparent from the data of Table 4 that the compression of modulus of the polymeric scaffold is lowered as the porosity increases. An excellent compression of modulus was obtained when the mass ratio of salt to PLLA was 10:1.

TEST EXAMPLE I

To confirm the suitability to three-dimensional cell culture of the porous, polymeric scaffold prepared in Example 2, rat hepatocytes were transplanted into the porous, polymeric scaffold according to the teaching of Mooney (P. M. Kaufmann, S. Heimrath, B. S. Kim, D. J. Mooney, Cell Transplantation (1997) 6, 5, 463–468). The transplantation efficiency was measured to be about 90–98%, indicating that the porous scaffold is of a suitable structure for cell transplantation. Detailed results are given in Table 5, below.

An MTT (3-(4,5-dimethylthiazol-2-yl)-2,5-diphenyltetrazolium bromide) assay was conducted to analyze the activity of the hepatocytes adherent to the scaffold. To this end, the cells were cultured for 24 hours at 37° C. at the atmospheric pressure in a mixed atmosphere of 95% $O_2$ and 5% $CO_2$. When hepatocytes were transplanted at a population of $7 \times 10^4$ cells/device, the activity was about 40% while a population of $4.8 \times 10^5$ cells/device resulted in 30%. Thus, the activity of the hepatocytes was gradually decreased as greater numbers of cells were transplanted.

Following well-known techniques (P. O. Seglen, Methods Cell. Biol. (1976) 13, 29–83; J. C. Y. Dunn, R. G. Tompkins, M. L. Yarmush, Biotechnol. Prog. (1991) 7, 237–245), an examination was made of the viability of the rat hepatocytes. After being separated from the porous polymeric scaffold, the cells were found to show a viability of about 90% as measured by a trypan blue exclusion test.

TABLE 5

Transplantation Efficiency of Cells

| Cell No./device | $7 \times 10^4$ | $1.4 \times 10^5$ | $2.8 \times 10^5$ | $4.8 \times 10^5$ |
|---|---|---|---|---|
| Efficiency (%) | 93.97 ± 0.22 | 90.29 ± 1.31 | 97.72 ± 0.82 | 97.93 ± 0.82 |

EXAMPLE III

Preparation of Porous Scaffold from Poly(D,L-lactic-co-glycolic Acid) through Polymeric Solution In chloroform, poly(D,L-lactic-co-glycolic acid) (PLGA) 65/35 with a weight average molecular weight of 180,000 was dissolved at an amount of 30% by weight To the resulting polymeric solution of high viscosity, ammonium bicarbonate particles ranging, in size, from 180 to 300 μm were added at mass ratios of 1:10, 1:15 and 1:20 polymer:salt, respectively, followed by homogeneously mixing to yield polymer/salt/solvent gels.

After being introduced into a Teflon mold which was 2 mm thick with a diameter of 5 mm, the gels each were deprived of the solvent methylene chloride by evaporation at the atmospheric pressure. Each of the polymer/salt mixtures separated from the mold was mixed to 3 liters of citric acid solutions of various concentrations (20%, 40%, 60%, supersaturated), and stirred to effervesce the salt. After completion of the effervescence, the porous polymeric scaffolds thus prepared were drawn off, washed with distilled water and dried in a vacuum drier.

With the aid of a mercury intrusion porosimetry (Porous Materials Inc., Ithaca, N.Y.), the scaffolds were measured for porosity and total pore volume, and the results are summarized in Table 6, below.

TABLE 6

Porosity and Pore Volume of Polymeric Scaffold

| Citric Acid Conc. (%) | Pore Diameter (μm) | Pore Volume (cc/g) | Porosity (%) |
|---|---|---|---|
| 20 | 122.03 ± 22.56 | 8.0603 | 98.03 |
| 40 | 149.49 ± 36.24 | 8.396 | 98.04 |
| 60 | 163.44 ± 0.74 | 9.2803 | 98.11 |
| Supersaturated | 186.24 ± 22.86 | 9.9842 | 98.64 |

Figure 3:
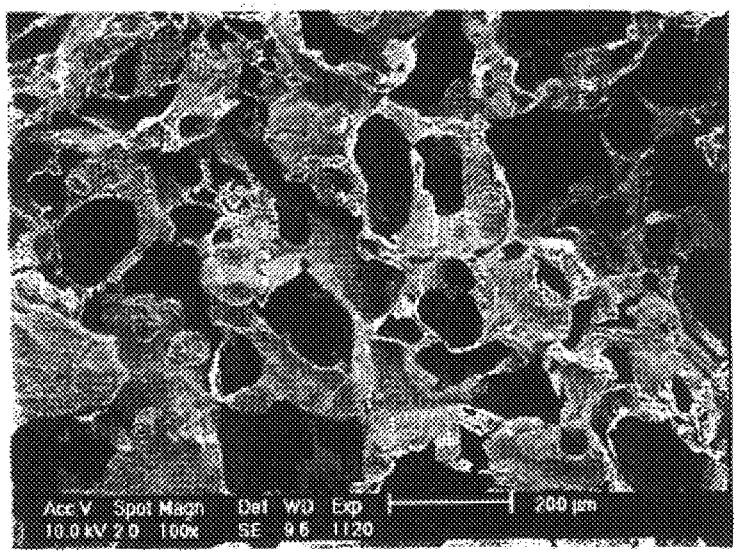
FIG. 3 is a magnified SEM photograph showing the surface of the poly(D,L-lactic-co-glycolic acid) based, porous scaffold prepared in Example III.
Figure 4A:
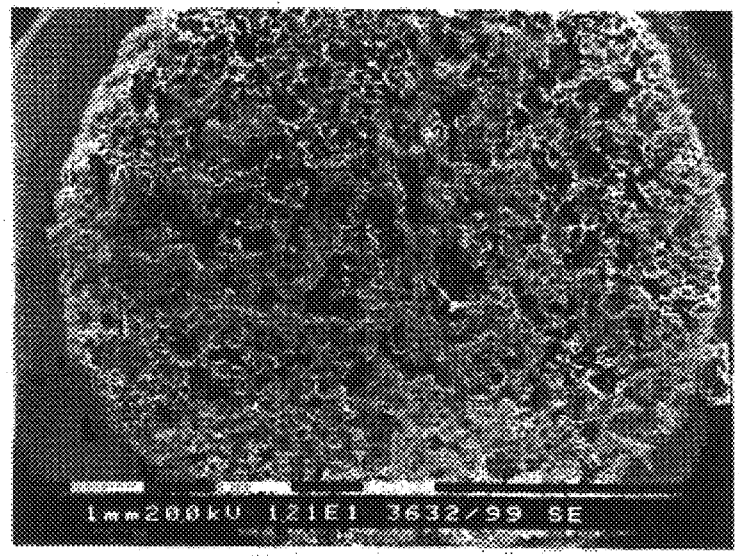
FIG. 4a is a SEM photograph showing the surface of the poly(D,L-lactic-co-glycolic acid) based, porous scaffold 2 mm thick with a diameter of 10 mm, prepared in Example IV
Figure 4B:
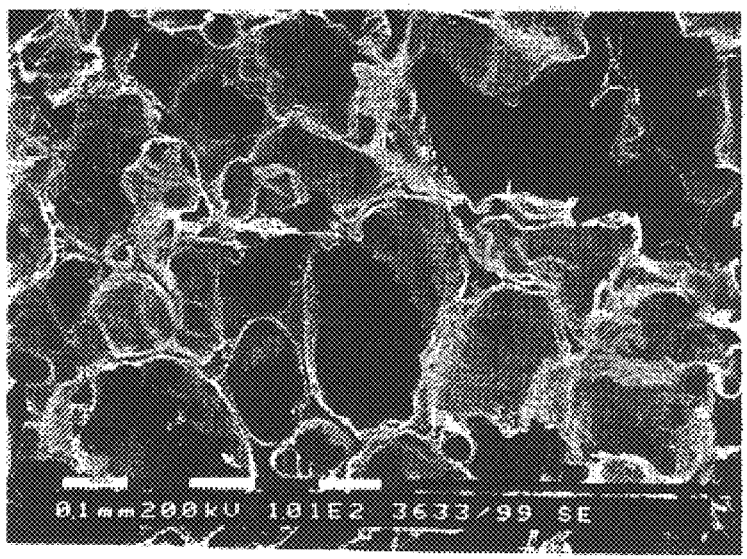
Figure 4C:
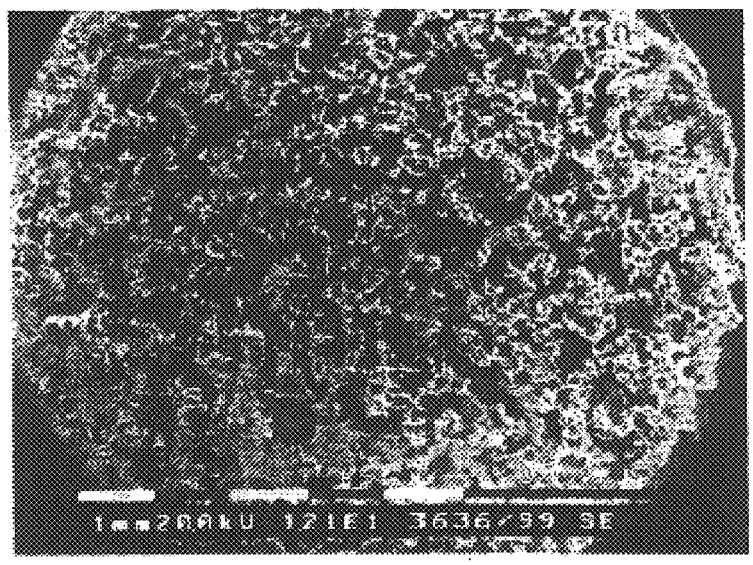
FIG. 4c is a SEM photograph showing the surface of the poly(D,L-lactic-co-glycolic acid) based, porous scaffold 5 mm thick with a diameter of 10 mm, prepared in Example IV
Figure 4D:
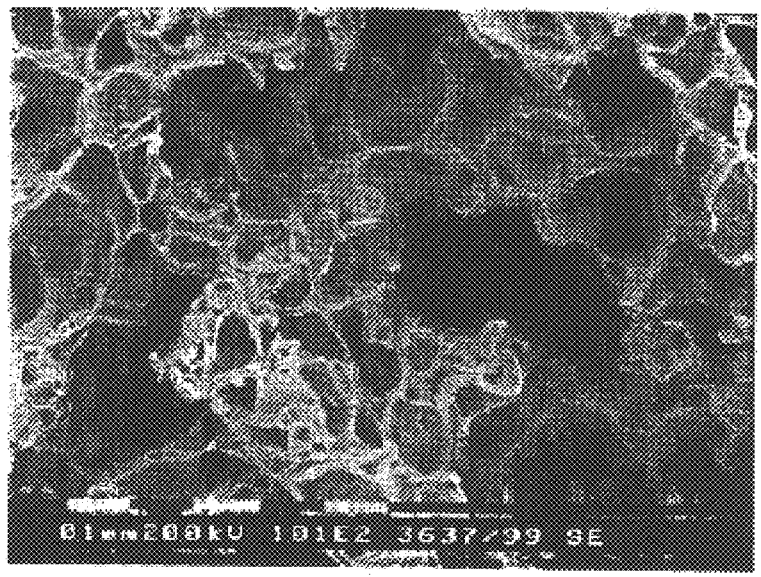
FIG. 4d is a magnified photograph of FIG. 4c.
Figure 5A:
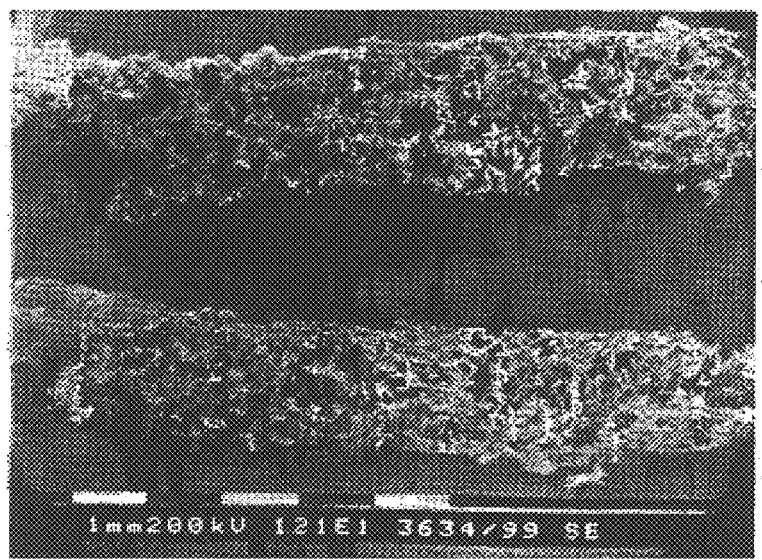
FIG. 5a is a SEM photograph showing the cross section of the poly(D,L-lactic-co-glycolic acid) based, porous scaffold 2 mm thick with a diameter of 10 mm
Figure 5B:
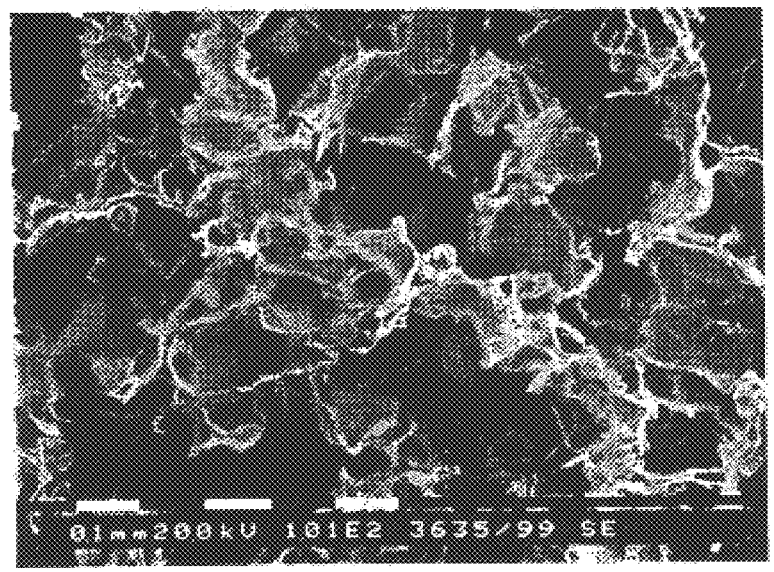
Figure 5C:
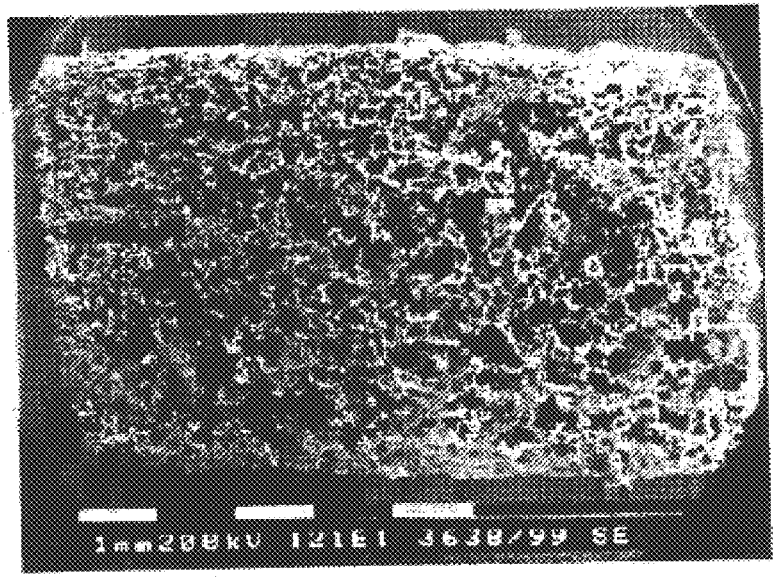
FIG. 5c is a SEM photograph showing the cross section of the poly(D,L-lactic-co-glycolic acid) based, porous scaffold 5 mm thick with a diameter of 10 mm
Figure 5D:
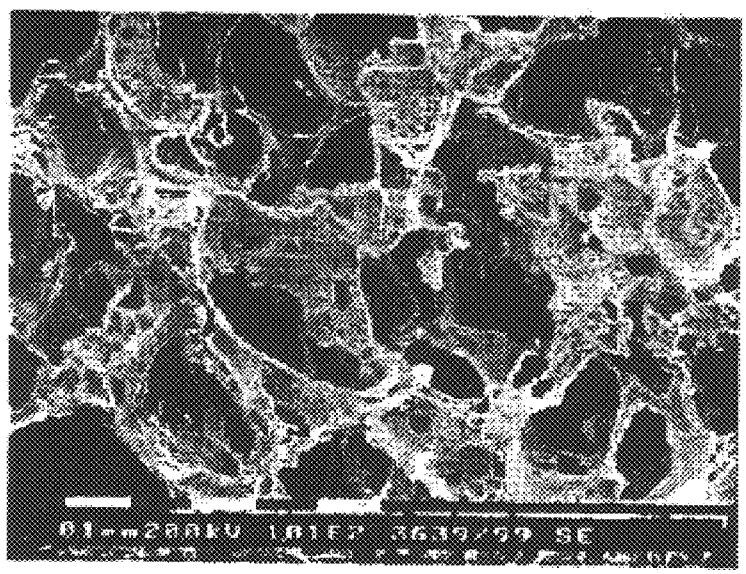
FIG. 5d is a magnified photograph of FIG. 5c.

An observation was made of the whole figures, and surface and cross section structures of the scaffolds, and the configuration of their inner pores through scanning electron microscopy (SEM) (Phillips 535M) and the results are given in FIG. 3.

Before the observation, the polymeric scaffolds were coated with gold in an argon atmosphere at 5 psi for 5 min under an electric field of 5 mA by using a sputter (Hummers, techniques U.S.A.).

A measurement was also made of the compression of modulus of the porous polymeric scaffolds prepared above. In this regard, the Instron 5538 was used to descend a load cell of 10 newton (N) at a speed of 2 mm/min vertically on a scaffold specimen, which was of a cylindrical shape 12 mm high with a diameter of 6 mm according to ASTM F451-95. The results are given, along with the porosity, in Table 7, below.

TABLE 7

Porosity and Compression of Modulus of Polymeric Scaffold

| Salt:Polymer (weight ratio) | Porosity (%) | Compression of Modulus (kPa) |
|---|---|---|
| 10:1 | 98.64 | 29.24 ± 0.40 |
| 15:1 | 98.92 | 16.45 ± 7.75 |
| 20:1 | 99.11 | 11.91 ± 0.54 |

As demonstrated in Table 6, higher concentrations of citric acid cause the salt to undergo more active effervescent reaction, resulting in greater increase in pore size and porosity. In addition, it is also recognized from the data of Table 7 that increasing the salt ratio to the polymer results in increasing the porosity while reducing the compression of modulus of the polymeric scaffold. That is, an increase in the porosity leads to a reduction in the compression of modulus of the porous scaffold.

EXAMPLE IV

Preparation of Porous Scaffold from Poly(D,L-lactic-co-glycolic Acid) through Polymer Precipitation A solution of poly(D,L-lactic-co-glycolic acid) (PLGA) 65/35, as used in Example III, in chloroform was added with an excess of ethanol and allowed to stand for 10 min to precipitate the polymer. After concentration, the polymeric precipitate maintained itself in a gel phase.

To the polymeric precipitate free of ethanol, ammonium bicarbonate particles ranging, in size, from 180 to 300 μm were added at a mass ratio of 1:10 polymer:salt. The polymer/salt/solvent gel slurry prepared contained an even less amount of organic solvent than did that of Example III.

After being introduced into two Teflon molds which were 2 mm and 5 mm in thickness with a diameter of 5 mm, respectively, the gel was deprived of the solvent by evaporation at the atmospheric pressure. The polymer/salt mixtures separated from the molds were mixed to 3 liters of supersaturated citric acid solution and stirred to effervesce the salt. After completion of the effervescence, the porous polymeric scaffolds thus prepared were drawn off, washed with distilled water and dried in a vacuum drier.

An observation was made of the whole figures, and surface and cross section structures of the scaffolds, and the configuration of their inner pores through a scanning electron microscope, as in Example III and the results are given in FIGS. 4 and 5. As shown in these figures, the porous scaffolds prepared according to the invention have pores of uniform sizes superior in interconnectivity and uniformly distributed over the themselves regardless of the pore sizes.

EXAMPLE V

Porous polymeric scaffolds were prepared in similar manners to that of Example IV, except that PLGA 50/50 and PLGA 75/25 were used instead of the biodegradable polymer PLGA 65/35. With the aid of a mercury intrusion porosimetry, the polymeric scaffolds were measured for porosity, pore diameter and surface area and the results are given in Table 8, below.

TABLE 8

Pore Diameter, Porosity and Surface Area of Polymeric Scaffold

| Scaffold | Pore Diameter ($\mu$m) | Porosity (%) | Surface Area ($m^2/g$) |
| --- | --- | --- | --- |
| PLGA 50:50(3 mm) | 121.59 | 86.60 | 89.21 |
| PLGA 65:35(3 mm) | 206.4 | 89.21 | 89.89 |
| PLGA 65:35(3 mm) | 210.51 | 88.73 | 91.96 |
| PLGA 75:25(3 mm) | 199.27 | 89.89 | 93.49 |
| PLGA 75:25(3 mm) | 208.71 | 91.96 | 91.15 |

Apparent from the results of Table 8 is that no big differences in porosity and total pore volume exist between porous polymeric scaffolds prepared through polymer precipitation and polymer solution.

The process described in Example IV has an advantage over that of Example III in that even smaller amounts of inorganic solvents are contained in the polymer/salt/inorganic solvent gels and thus, can be more readily removed, thereby allowing various drugs to be introduced effectively thereinto, later.

TEST EXAMPLE II

Cell Culture Using Poly(D,L-lactic-co-glycolic Acid) Porous Scaffold

Figure 6:
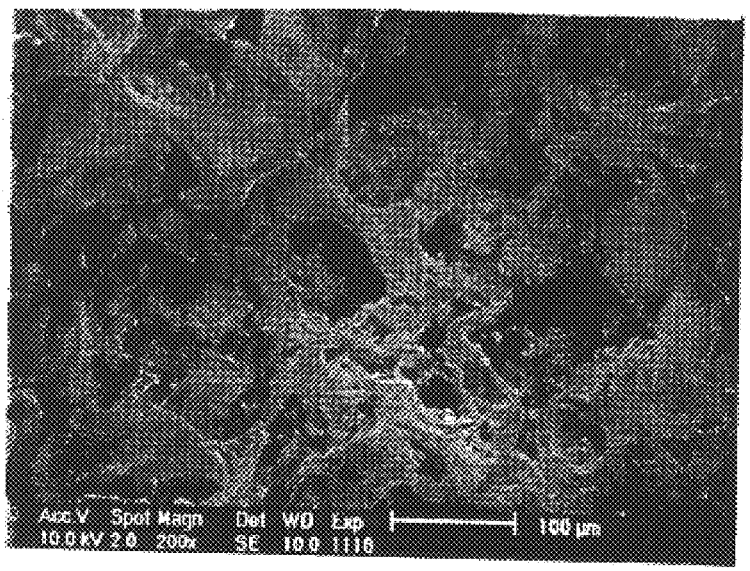
FIG. 6 is a SEM photograph showing the rat hepatocytes which have been inoculated on the porous scaffold of FIG. 3 and cultured for 7 days.
Figure 7:
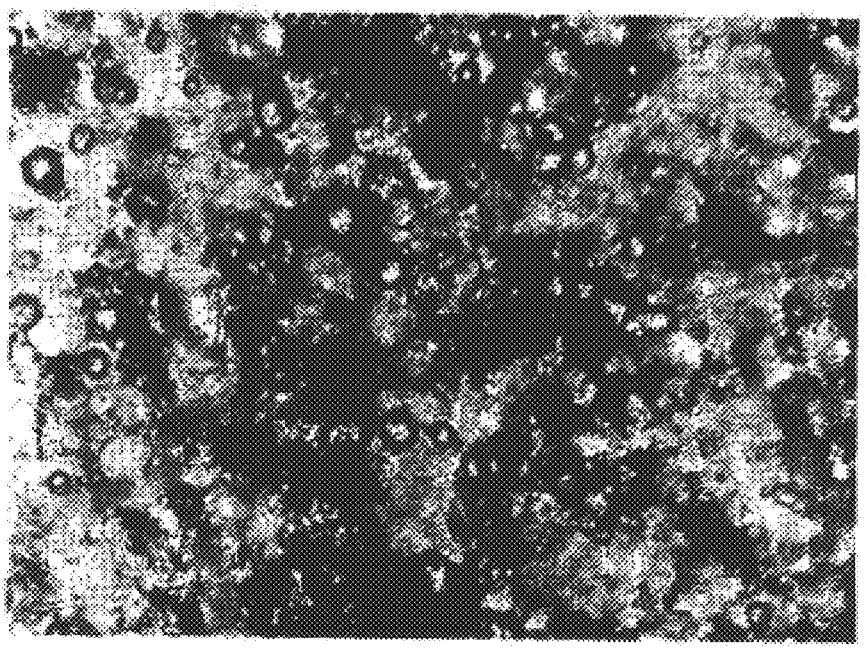
FIG. 7 is an optical microphotograph showing the distribution of viable hepatocytes after an MTT assay for the determination of viability of cultured cells.

To confirm the suitability to three-dimensional cell culture of the porous, polymeric scaffolds prepared, rat hepatocytes were transplanted into the porous, polymeric scaffold according to a well-known technique (P. M. Kaufmann, et al., Cell Transplantation (1997) 6, 5, 463–468) and cultured for 7 days (FIG. 6). The number of the hepatocytes to be transplanted was in the range of $7\times10^4$ to $8\times10^4$ per porous scaffold. As many hepatocytes as in this range were found to be about 90–95% in transplantation efficiency. This was believed to result from the uniform distribution of the introduced hepatocytes over the porous scaffolds which were superior in the interconnectivity among the pores. The porous polymeric scaffolds into which the hepatocytes were transplanted were incubated for 7 days at 37° C. in the presence of 5% $CO_2$ in an incubator to examine the viability of the cells. In this regard, an MTT (3-(4,5-dimethylthiazol-2-yl)-2,4 diphenyltetrazolium bromide) assay was conducted. As shown in FIG. 7, viable cells were uniformly distributed over the whole scaffold structure.

In Table 9, below, cell viability for 7 days of incubation is given, along with secreted albumin amount, an indicator for the differentiating function of hepatocytes.

TABLE 9

Cell Viability and Secreted Albumin Amount of Hepatocytes Cultured in Porous Polymeric Scaffolds for 7 Days

| Nos. of Inoculated Cells ($10^4$/scaffold) | Viability (% viable cell No. at initial stage) | Amount of Albumin Secreted (pg/cell) |
| --- | --- | --- |
| 14 | 37.924504 | 46.690272 ± 4.049649 |
| 28 | 26.150778 | 35.523805 ± 6.834733 |
| 42 | 25.298302 | 37.590655 ± 2.815256 |
| 56 | 23.543620 | 34.181293 ± 0.199821 |

According to the data of Table 9, the number of viable cells was reduced by about 20–30% after 7 day-incubation in the porous polymeric scaffold and both the viability and the albumin secretion of hepatocytes cultured in the scaffold are lowered as the number of the inoculated cells increases.

INDUSTRIAL APPLICABILITY

As described hereinbefore, the present invention provides a method for preparing biodegradable and biocompatible, porous polymeric scaffolds which are so porous and interconnective among pores as to accommodate and culture cells isolated from the tissues which are to be artificially regenerated in vitro, such as cartilage, bone, liver, heart valve, gastrointestinal duct, urethral canal, etc. The scaffolds serve as excellent matrixes for the artificial culture of various cultures.

In addition, based on the pore formation by the effervescence of salts in the gels prepared from biodegradable polyester polymer and effervescent salt mixtures, the method has an advantage of easily controlling the pore size and porosity of the three-dimensional porous, polymeric scaffolds by controlling the amount and size of the effervescent salts and the concentration of the acidic aqueous solutions by which the effervescence and leaching-off of the salts are induced.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing a biodegradable and biocompatible, porous, polymeric scaffold for tissue engineering, comprising the steps of:
   dissolving a biodegradable polymer in an organic solvent to prepare a polymeric solution of high viscosity;
   homogeneously mixing an effervescent salt in the polymeric solution to give a polymer/salt/organic solvent mixed gel;
   removing the organic solvent from the polymer/salt/organic solvent mixed gel to produce an organic solvent-free polymer/salt gel slurry;
   submerging the organic solvent-free polymer/salt gel slurry in a hot aqueous solution or acidic solution to cause the salt to effervesce at room temperature to form a three-dimensional polymeric structure; and washing the three-dimensional polymeric structure with distilled water and freeze-drying the washed polymeric structure.

2. A method as set forth in claim 1, further comprising the step of precipitating and concentrating the polymer in an organic solvent which does not dissolve the polymer, after the dissolving step.

3. A method as set forth in claim 1, wherein the biodegradable polymer is an aliphatic polyester selected from the group consisting of poly (L-lactic acid), poly (D,L-lactic acid), poly (glycolic acid), poly (D,L-lactic-co-glycolic acid), poly (caprolactone), poly (hydroxy butyrate), and copolymers of those polymers.

4. A method as set forth in claim 1, wherein the organic solvent for use in dissolving the biodegradable polymer is selected from the group consisting of methylene chloride, chloroform, acetone, dimethylsulfoxide, dimethylformamide, N-methylpyrrolidone, dioxane, tetrahydrofuran, ethylacetate, methylethylketone, and acetonitrile.

5. A method as set forth in claim 2, wherein the organic solvent that does not dissolve the polymer is selected from the group consisting of ethanol, methanol, aqueous ethanol, ethyl ether, diethyl ether, hexane, petroleum ether, and aqueous petroleum ether.

6. A method as set forth in claim 1, wherein the effervescent salt is selected from the group consisting of ammonium carbonate, ammonium bicarbonate, sodium carbonate, and sodium bicarbonate.

7. A method as set forth in claim 1, wherein the acidic aqueous solution used in effervescing the salt in the polymer/salt gel slurry is an aqueous solution of citric acid, hydrochloric acid, acetic acid, formic acid, tartaric acid, salicylic acid, benzoic acid, or glutamic acid.

8. A method as set forth in claim 1 or 3, wherein the biodegradable polymer ranges, in molecular weight, from 5,000 to 500,000.

9. A method as set forth in claim 1 or 6, wherein the effervescent salt ranges, in particle size, from 100 to 500 $\mu$m.

10. A method as set forth in claim 1 or 6, wherein the effervescent, salt is added at such an amount that the weight ratio of the salt to the polymer is in the range from 1:1 to 1:100.

11. A method as set forth in claim 1 or 7, wherein the acidic aqueous solution is prepared by dissolving the acid in water or in an aqueous solution saturated with an organic solvent that dissolves the biodegradable polymer, said solvent selected from the group consisting of methylene chloride, chloroform, acetone, dimethylsulfoxide, dimethylformamide, N-methylpyrrolidone, dioxane, tetrahydrofuran, ethylacetate, methylethylketone, and acetonitrile.

12. A method as set forth in claim 1 or 7, wherein the acidic aqueous solution ranges in acid concentration from 1% to supersaturation.

* * * * *

UNITED STATES PATENT AND TRADEMARK OFFICE
CERTIFICATE OF CORRECTION

PATENT NO.    : 6,586,246 B1
DATED         : July 1, 2003
INVENTOR(S)   : Jun-Jin Yoon, Tae-Gwan Park and Yoon-Sung Nam It is certified that error appears in the above-identified patent and that said Letters Patent is hereby corrected as shown below:

<u>Title page,</u>
Item [73], Assignee, delete "Innotech Medical, Inc., Daejon (KR)" and insert therefore -- $^1/_2$ interest to Korean Advanced Institute of Science & Technology (KAIST) and $^1/_2$ interest to Innotech Medical, Inc. (Innotech), Daejon (KR) --

<u>Column 12,</u>
Line 14, delete "," between "effervescent" and "salt"

Signed and Sealed this

Twenty-fifth Day of November, 2003

JAMES E. ROGAN
*Director of the United States Patent and Trademark Office*